United States Patent [19]

Gundelfinger

[11] 4,068,528
[45] * Jan. 17, 1978

[54] TWO POSITION ROTARY VALVE FOR INJECTING SAMPLE LIQUIDS INTO AN ANALYSIS SYSTEM

[75] Inventor: Richard Gundelfinger, Oakland, Calif.

[73] Assignee: Rheodyne Incorporated, Berkeley, Calif.

[*] Notice: The portion of the term of this patent subsequent to Aug. 8, 1993, has been disclaimed.

[21] Appl. No.: 676,424

[22] Filed: Apr. 13, 1976

Related U.S. Application Data

[63] Continuation-in-part of Ser. No. 650,469, Jan. 19, 1976, abandoned, which is a continuation-in-part of Ser. No. 609,394, Sept. 2, 1975, Pat. No. 3,961,394.

[51] Int. Cl.² ............................................. G01N 1/10
[52] U.S. Cl. ................................................ 73/422 GC
[58] Field of Search .................................... 73/422 GC

[56] References Cited

U.S. PATENT DOCUMENTS

| | | | |
|---|---|---|---|
| 3,346,486 | 10/1967 | Winter | 73/422 GC |
| 3,411,525 | 11/1968 | Auger | 73/422 GC |
| 3,827,303 | 8/1974 | Shiina | 73/422 GC |
| 3,961,534 | 6/1976 | Gundelfinger | 73/422 GC |
| 4,022,065 | 5/1977 | Ramin | 73/422 GC |

*Primary Examiner*—S. Clement Swisher
*Attorney, Agent, or Firm*—Lindenberg, Freilich, Wasserman, Rosen & Fernandez

[57] ABSTRACT

Several embodiments of a two-position rotary valve for injecting a liquid sample into a stream of solvent, flowing through a liquid chromatographic column, are disclosed. The valve is switchable between a Load position and an Inject position. The valve includes a needle cavity axially extending along the valve's rotor axis of rotation. The needle cavity is designed to accommodate a syringe needle from which a sample is loaded into one end of a sample loop which is externally connected to the valve, while the opposite end of the loop is vented to the atmosphere, when the valve is in the Load position. This facilitates the loading of the sample into the sample loop through the needle cavity at atmospheric pressure with a conventional syringe needle. In the Inject position solvent is made to flow through the sample loop in order to eject the sample from the loop and inject it onto the column. Sample ejection from the loop may take place from the same loop end through which the sample was loaded into the loop or from the loop's opposite end.

16 Claims, 15 Drawing Figures

TWO POSITION ROTARY VALVE FOR INJECTING SAMPLE LIQUIDS INTO AN ANALYSIS SYSTEM

CROSS-REFERENCES TO RELATED APPLICATIONS

This application is a Continuation-in-Part of application Ser. No. 650,469, filed Jan. 19, 1976, now abandoned, which is a Continuation-in-Part of application Ser. No. 609,394, filed Sept. 2, 1975, now patent no. 3,961,394.

BACKGROUND OF THE INVENTION

1. Field of the Invention

The present invention generally relates to a valve for injecting a sample into a flowing stream and, more particularly, to a two-position rotary valve for injecting a liquid sample into a high pressure stream of liquid by means of a conventional low pressure volumetric syringe.

2. Description of the Prior Art

In the field of liquid chromatography, the contents of a liquid sample, which consists of unknown quantities of compounds, is analyzed by injecting the sample in a stream of a suitable eluting solvent, which passes through the chromatographic column and therefrom to an appropriate detector. Typically, the solvent from an appropriate source is pumped to the column by a pump, e.g., a constant flow pump. Modern columns generate relatively high back pressures under normal operation, e.g., 2000 psi and above.

For many years the fixed loop sample injection valve has been used in high pressure liquid chromatography because of its convenience of use, reliability and precision. Its major disadvantages are that a considerable amount of sample is wasted in the process of sample loading to insure that the sample loop is completely filled. Also, sample size can be changed only by changing the loop size. Syringe injection methods have been employed to circumvent these problems. The use of an elastomeric septum to permit direct sample injection by means of a syringe has the disadvantages of incompatibility with many eluting solvents, limitation of operating pressures to approximately 1000 psi and the requirement of special syringes with high pressure capability. Septumless injection devices have been designed for use with syringes. However, these devices require stopping the solvent flow for a reasonably long period, which is undesirable, since it usually leads to problems in stabilizing the detector signal.

Thus, a need exists for a simple, yet highly reliable sample injecting device which eliminates the disadvantages of each of the above described methods, while maintaining the advantages of reliable high pressure capability, convenient use of conventional syringes, variability of sample size, minimal sample waste, solvent compatibility and uninterrupted or substantially uninterrupted solvent flow.

SUMMARY OF THE INVENTION

One embodiment of the present invention comprises a two-position rotary valve with which a restrictor loop and a sample loop are associated. The restrictor loop is connected to the valve so that irrespective of the valve position the restrictor loop provides an uninterrupted path for solvent to flow from an appropriate solvent source to the liquid chromatographic column. In one embodiment of the valve the downstream end of the sample loop is directly connected to a needle cavity which extends along the valve rotor, and is axially aligned with the valve's axis of rotation. The upstream end of the sample loop is connected to one of the external threaded fitting ports of the valve stator. In one valve position, defined as the Load position, the sample loop upstream end is connected through the valve rotor to a vented port of the stator, which is at atmospheric pressure. Thus, in the Load position, the sample loop and the needle cavity are at atmospheric pressure. In this position, the sample is loaded into the needle cavity and therefrom into the downstream end of the sample loop from a syringe needle, which extends into the needle cavity through a needle cavity seal. After sample loading, the needle is withdrawn and a wire-shaped plug of diameter substantially equal to that of the syringe needle is inserted through the seal into the needle cavity. The seal with the plug is capable of withstanding high pressure.

After the plug insertion the valve is switched to its second position, defined as the Inject position. In this position the upstream end of the sample loop is separated from the vented port of the stator and is in turn connected to the stator port through which solvent is supplied to the valve. The downstream end of the needle cavity is in communication with the stator port which is connected to the column. Thus, in the Inject position solvent flows in parallel in the restrictor loop and in the serially connected sample loop and needle cavity from the solvent source to the column. The sample, previously loaded into the downstream end of the sample loop, is injected onto the column with minimal delay by the solvent flowing in the sample loop and the needle cavity to the column.

Other embodiments of the invention, in which both ends of the sample loop are connected to stator ports with and without the restrictor loop are also described. In one of these embodiments the needle cavity is outside the solvent flow path in the Inject position.

The novel features of the invention are set forth with particularity in the appended claims. The invention will best be understood from the following description when read in conjunction with the accompanying drawings.

DESCRIPTION OF THE PREFERRED EMBODIMENTS

Figure 1:
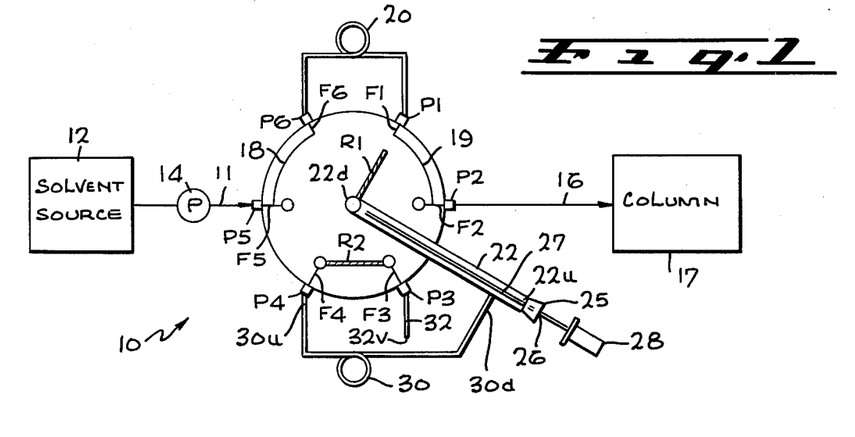
FIGS. 1 and 2 are essentially simplified combination schematic and block diagrams of the valve in the Load position.

Attention is directed to FIG. 1 which is a modified schematic diagram of one embodiment of the novel two-position rotary switching valve 10, shown in the Load position. The valve's stator includes six external threaded fitting ports, designated P1-P6 for external tubing connections. These external ports are respectively in communication with internal flow passages F1-F6 in the stator. In the particular example, port P5 is shown connected to a tubing or line 11 through which solvent from a solvent source 12 is pumped by a pump 14 to the valve. Coupled to external port P2 is a tubing or line 16 through which solvent with or without sample flows from the valve 10 to a liquid chromatographic column 17.

The stator has internal slots 18 and 19 of effectively zero dead volume. Slot 18 interconnects the stator flow paths F5 and F6, thereby providing a flow path from external port P5 to port P6, while slot 19 interconnects the stator flow paths F1 and F2, thereby providing a flow path between external ports P1 and P2. Externally connected between ports P6 and P1 is a coiled length of a capillary tubing 20, hereinafter referred to as the restrictor loop 20, which is chosen to provide a selected resistance to flow therethrough. Since port P6 is connected to port P5 and port P1 is connected to port P2, a permanent path for the flow of eluting solvent, which enters the valve through port P5 and exits it through port P2 is provided between the source 12 and the column 17. This flow is uninterrupted and is independent of valve position. In the Load position all of the eluting solvent flows to the column 17 through the restrictor loop 20.

The novel valve 10 includes a rotor which defines an axial needle cavity 22. The downstream end of cavity 22, designated 22d, is in communication with one end of a flow passage R1 in the rotor. In order to distinguish between the paths of solvent flow in the stator and the rotor, those in the stator will be referred to as flow paths while those in the rotor will be referred to as flow passages. The other end of passages R1 in the Load position is not in communication with any of the flow paths in the stator. Thus, in this position end 22d of the needle cavity 22 can be thought of as being closed off. The other end of the needle cavity 22, hereinafter referred to as the upstream end 22u, is closed or sealed off by an adjustable flexible seal 25 which defines an opening 26 through which either a needle 27 of a syringe 28 or a wire-shaped plug, is insertable, as will be described hereinafter in detail.

Associated with the valve 10 is a second external coiled tubing, defining a sample loop 30. Its upstream end 30u is connected to external port P4 and its downstream end 30d is connected to needle cavity 22 near its end 22u at which the seal 25 is located. A vent tubing 32 is connected at one end to port P3 while its other end 32v is assumed to be open to the atmosphere. The rotor defines a second flow passage R2. The ends of the stator flow paths, such as F2-F5 which may come in contact with the rotor flow passages are shown as small circles. In the Load position, as shown in FIG. 1, it provides a flow path between ports P3 and P4 via F3 and F4. Thus, the sample loop 30 and the needle cavity 22 are at atmospheric pressure. This facilitates the use of a conventional syringe, rather than a high pressure syringe, to load a liquid sample into the sample loop 30.

Figure 2:
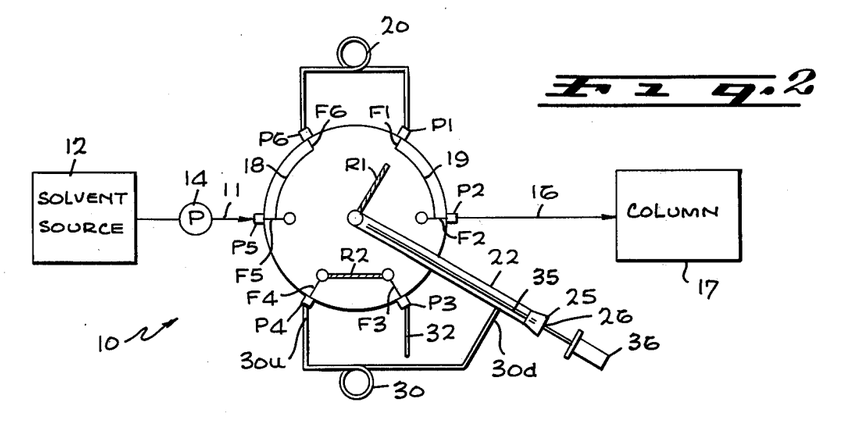

In practice, in the Load position the syringe needle 27 is inserted into the cavity 22 through the opening 26 in seal 25. The desired volume of sample, preferably read off the syringe markings, is loaded into the cavity 22 through the needle 27. The diameter of the needle cavity 22 is chosen with respect to the outer diameter (OD) of the needle so that with cavity end 22d deemed as closed off, practically all of the sample passes out of the needle tip and is loaded into the sample loop 30 through its downstream end 30d. After sample loading, the syringe needle 27 is withdrawn through seal opening 26 and a wire-shaped plug 35 of a diameter substantially equal to that of the needle 27 is inserted into the cavity 22. FIG. 2 is the same as FIG. 1, showing the valve 10 in the Load position, except that the plug 35 is shown in cavity 22 instead of the needle 27. The plug end, external to seal 26, terminates in a plug holder 36 which is lockable, as will be explained hereinafter, so that when pressure is built up in the needle cavity 22 the plug 35 is prevented from being ejected out of the cavity through the seal opening 26. The valve including seal 25 with the plug 35 therein are capable of withstanding relatively high pressures, e.g., 7000 psi.

Figure 3:
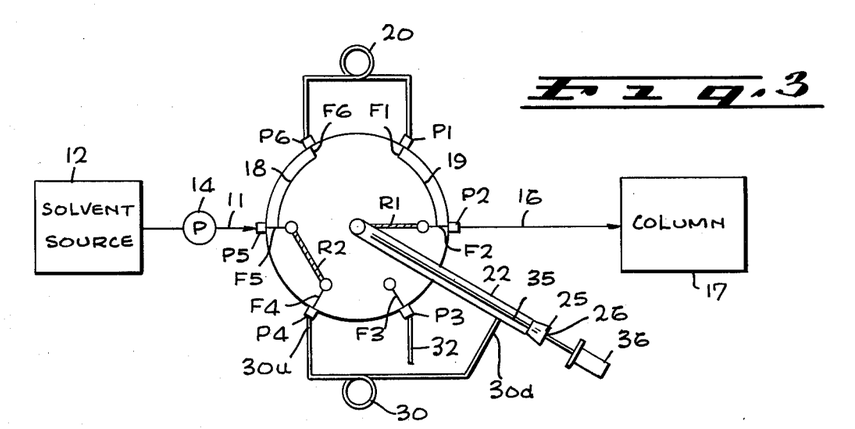
FIG. 3 is essentially a simplified combination schematic and block diagram of the valve in the Inject position.

After the plug holder 36 is locked the valve is switched to its second position, defined as the Inject position, by rotating the rotor with respect to the stationary stator. FIG. 3 shows the valve in the Inject position. In this position rotor flow passages R1 connects the downstream end 22d of needle cavity 22 through the stator internal flow path F2 to port P2, to which the downstream line 16 is connected. Also in the Inject position the rotor flow passage R2 connects port P4 to port P5 (via F4 and F5). Thus, the upstream end 30u of the sample loop is connected to the upstream line 11, through which solvent is supplied to the valve. Consequently, solvent flows between upstream port P5 to downstream port P2 and therefrom to the column 17 through the sample loop 30 and the needle cavity 22, forcing the previously loaded sample ahead of it. Since the sample was loaded into the sample loop through the loop's downstream end 30d, it flows onto the column 17 with minimal delay.

It should be stressed that while in the Inject position solvent flows through the sample loop and the needle cavity 22, forcing sample onto the column, the flow of solvent through the restrictor loop 20 continues uninterrupted. Thus, in the Inject position solvent flows in parallel in both the restrictor loop 20 and in the sample loop 30. The lengths and internal diameters (ID) of the two loops are chosen so that a desired solvent ratio flows in the two loops in the valve's Inject position.

In one embodiment, actually reduced to practice, the restrictor loop ID is about 0.012 inch and that of the sample loop is 0.020. In this embodiment $\frac{7}{8}$ of the solvent flows through the sample loop 30 while $\frac{1}{8}$ flows through the restrictor loop 20. It should be stressed however that in the Load position (FIGS. 1 and 2) all of the solvent flows only through the restrictor loop 20. The ID of the needle cavity 22 is made sufficiently large to accommodate syringe needles of different outside diameters. In the particular embodiment which was reduced to practice the ID of the needle cavity 22 is about 0.033 inch to accommodate needles of 0.018 inch to 0.028 inch outside diameter (OD).

Preferably the opening 26 of the seal should have an ID compatible with the outside diameter (OD) of the syringe needle 27, used to load the sample, and the plug 35, which is used to replace the needle prior to switching the valve to the Inject position. However, as will be described hereinafter the seal 25 is compressible so that the ID of opening 26 may be chosen to accommodate the largest needle to be used. The seal may be compressed to reduce the ID of opening 26 so as to accommodate therein needles and plugs of smaller OD, yet be able to withstand the high pressure, e.g., 7000 psi when solvent flows through the sample loop and the needle cavity.

Figure 4:
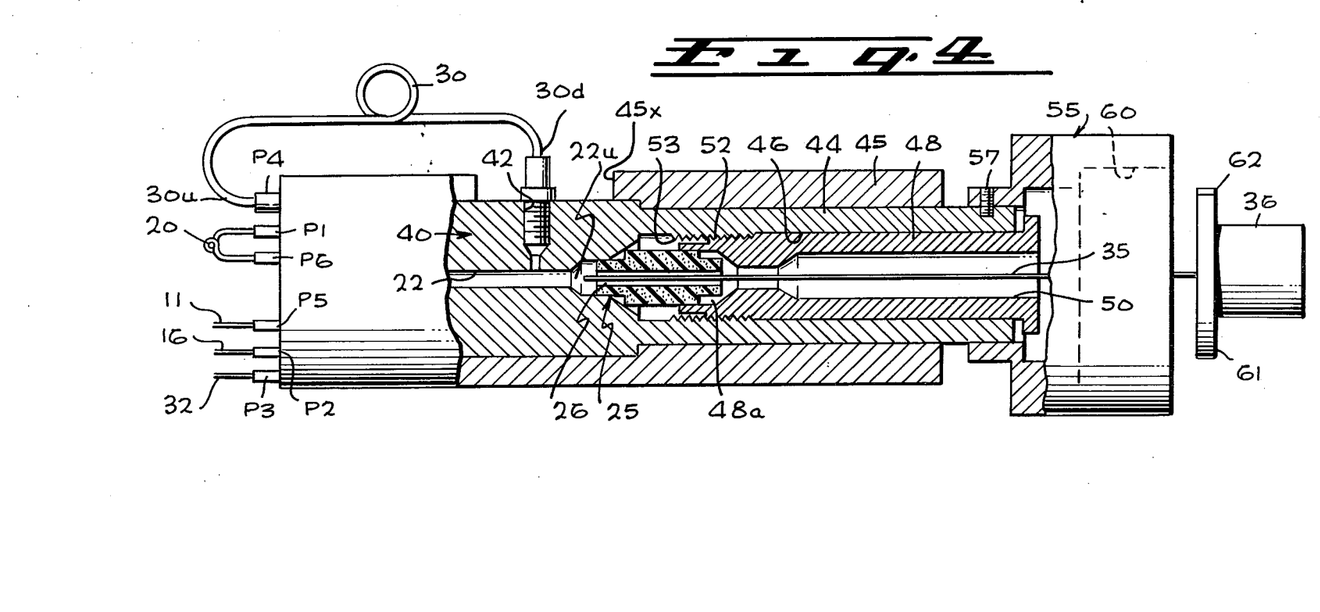
FIG. 4 is a simplified combination block and schematic diagram of one embodiment of the two-position rotary valve.

Attention is now directed to FIG. 4 which is a simplified combination side and cross-sectional view of one embodiment of the valve of the present invention. It is shown with the plug 35 partially inserted therein. In FIG. 4 numeral 40 designates the rotor with its axially aligned needle cavity 22. A threaded fitting port 42 extends from the cavity 22 to the rotor periphery. It is the downstream end 30d of the sample loop 30, which is connected to port 42. The rotor 40 and a rotor shaft 44 extending from rotor 40, are housed in the stator housing 45. The latter defines a slot 45X to provide access for the sample loop downstream end 30d to port 42.

The rotor shaft 44 has an axial opening 46, designed to accommodate a bushing 48 with an axial opening 50. A recess 48a in bushing 48 accommodates one end of seal 25. Threads 52 on the outer surface of bushing 48 are provided. These mesh with threads 53 in the inner surface of shaft 44. Thus, the bushing 48 is threadable in and out of the shaft 44. The seal 25, with its opening 26 aligned with cavity 22 and bushing opening 50, is supported at one end by the bushing 48 while its other end is accommodated near the upstream end 22u of cavity 22 in rotor 40.

The seal 25, which is flexible, is compressible as the bushing 48 is threaded into the shaft 44. When compressed the ID of its opening 26 decreases. Thus, the ID of opening 26 is controlled, so that with the plug 35 inserted therethrough the seal 25 together with the plug 35 effectively seal the upstream end 22u of the cavity 22 to prevent any leakage out of the cavity 22, even when solvent at high pressure flows through the cavity in the Inject position of the valve.

In practice, the plug 35 has an OD equal to that of the syringe needle to be used. The bushing 48 is threaded into the shaft 44 to compress the seal sufficiently to form a relatively tight fit between the seal 25 and either needle 27 or plug 35. In operation, with the valve in the Load position, the plug 35 is withdrawn and the syringe needle 27 is inserted into the cavity 22 to load the sample (see FIG. 1). Thereafter, the needle is withdrawn and replaced by the plug 35. The plug holder 36 is lockable in a valve knob 55 which is fastened to the rotor shaft 44 by set screws 57.

Figures 5, 6:
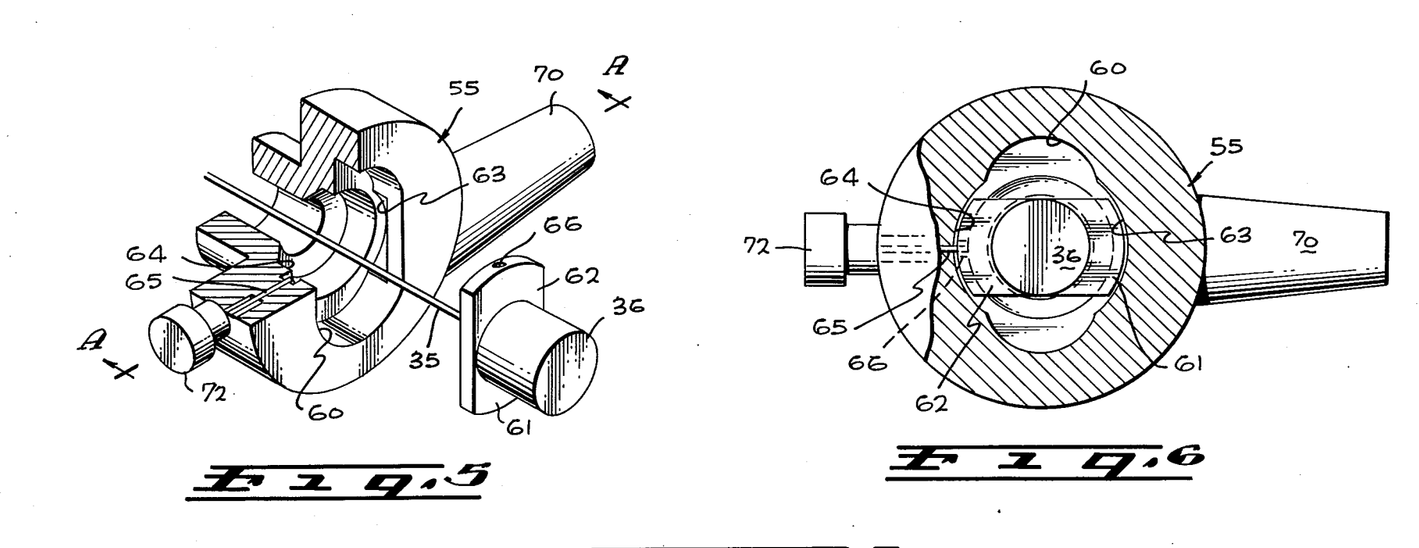
FIG. 5 is an isometric view of a valve knob, partially broken away, and a plug holder, useful in explaining certain aspects of the invention.
FIG. 6 is a cross-sectional view of the knob along lines A—A in FIG. 5, with the plug holder in a locked position.

One embodiment of the knob 55, which was actually reduced to practice, and the manner in which the plug holder is lockable therein may best be described in connection with FIGS. 5 and 6. FIG. 5 is an isometric view of the knob 55, partially broken away, and the plug 35 with its plug holder 36. FIG. 6 is a cross sectional view along lines A—A in FIG. 5, showing the plug holder in the locked position. The knob has an oval-shaped opening 60, whose center is axially aligned with opening 50 of bushing 48. One of the functions of opening 60 is to enable the plug holder 36, from which flanges 61 and 62 extend and which form part of the plug holder 36, to be inserted into the knob 55. The knob has a pair of recesses 63 and 64 which extend inwardly from opening 60 in a direction perpendicular to its major axis.

In operation to lock the plug holder 36 to the knob 55 the former is inserted through opening 60 and thereafter is rotated 90° so that flanges 61 and 62 are in recesses 63 and 64, respectively. The front end of a spring loaded pin 65 extends into recess 64 so that when the flange 62 is accommodated in recess 64 the front end of the pin 65 is engaged in a recess 66 in flange 62, thereby further securing the plug holder in the locked position.

As shown in these figures a handle 70 extends from knob 55 to facilitate the turning of the knob to switch the valve from one position to the other. Opposite handle 70 a pullable knob 72 is located. When pulled it retracts the pin 65 from recesses 64 and 66 thereby enabling the plug holder 36 to be rotated 90° and withdrawn from the knob through oval shaped opening 60.

It should be appreciated that with the two-position rotary valve of the present invention, as hereinbefore described, a sample can be loaded into a stream of solvent flow and thereafter inject the sample onto a liquid chromatographic column without interrupting the solvent flow. The sample is loaded into the sample loop when the valve is in the Load position, in which the pressure in the sample loop is at a low pressure, e.g., atmospheric pressure, as compared with the high pressure of the solvent fed from source 12. Consequently, a conventional syringe, rather than a high pressure syringe, can be used for sample loading. When the valve is switched to the Inject position (FIG. 3) solvent flows through the sample loop and forces the previously loaded sample ahead of it for injection onto the column. The sample loop 30, which is external to the valve, is chosen to be able to contain the largest volume of sample expected to be loaded, without any of the sample spilling over and being vented through vent end 32v. However, it should be pointed out that the sample loop need not be filled with the sample which is loaded into it through its downstream end. Any desired sample volume, from a few microliters ($\mu l$) up to the maximum capacity of the sample loop can be introduced by the conventional syringe. None of the sample is wasted and all of it gets injected onto the column.

To withstand high pressure, e.g., on the order of 7000 psi, the seal 25 is provided. Through its opening 26 a needle of a conventional syringe is inserted to load the sample. Then the needle is replaced by a wire-like plug, which together with the seal 25, effectively seal the upstream end of the needle cavity to withstand the high pressure in the latter without leaking, when the valve is switched to its Inject position. Both the syringe needle and the plug are easily insertable into the needle cavity through the seal which is accessible through an opening in the valve knob and an aligned opening in a bushing. The latter is threadable to the rotor shaft to appropriately compress the seal, so as to enable it, together with the plug 35, to withstand the high pressure when the valve is in the Inject position. It should thus be apparent that with the two-position rotary valve of the present invention, a sample can be injected with a conventional syringe for subsequent high pressure injection of the sample onto a column, without any loss of sample.

In the embodiment described in connection with FIGS. 1-3 it was assumed that the sample is loaded or introduced via the needle cavity 22 into the sample loop 30 through an end 30d (see FIG. 1), hereinbefore referred to as the downstream end. It was also assumed that in the Inject position the sample exits the sample loop 30 through the same end, i.e., end 30d. In such a case, the valve can be thought of as operating in a downstream mode since both sample loading and sample ejection from the sample loop take place from the same loop end.

If desired, when the valve is in the Inject position the sample may be injected onto the column through the end of the loop which is opposite the end through which the sample was loaded into the loop. In such a case, the valve can be viewed as operating in an upstream mode. This can be accomplished with the valve hereinbefore described by connecting the column 17 to port P5 with line 16, and the pump 14, which pumps solvent from source 12, to port P2 with line 11. In such a case in the Inject position (see FIG. 3) the solvent from source 12 will flow via port P2, rotor passageway R1 and needle cavity 22 into the sample loop 30 through loop end 30d. The solvent will push the sample ahead of it and exit the loop 30 through loop end 30u, which is connected to port P4. Therefrom it will flow through stator flow path F4, rotor flow passage R2, and F5 to port P5, to which the column is connected.

In the foregoing description it was assumed that the loop end 30d is directly connected to the needle cavity 22 near cavity end 22u (see FIGS. 1-3 and 4). In FIG. 4 port 42 is shown for connecting end 30d of the loop 30 to the needle cavity 22. Thus, in the foregoing described embodiment one end (30u) of the loop 30 is connected to a stator port (P4) and the other end (30d) is connected directly to the needle cavity which is part of the rotor. Such an arrangement may require a relatively long sample loop, which may be undesirable, particularly, if the valve is to be operated in an upstream mode and peak spreading is to be minimized. Also, the need for providing an opening 45x in the stator housing 45 (see FIG. 4) to provide access for loop end 30d to the needle cavity may be found to complicate the valve construction, and possibly increase its manufacturing cost.

Figure 7:
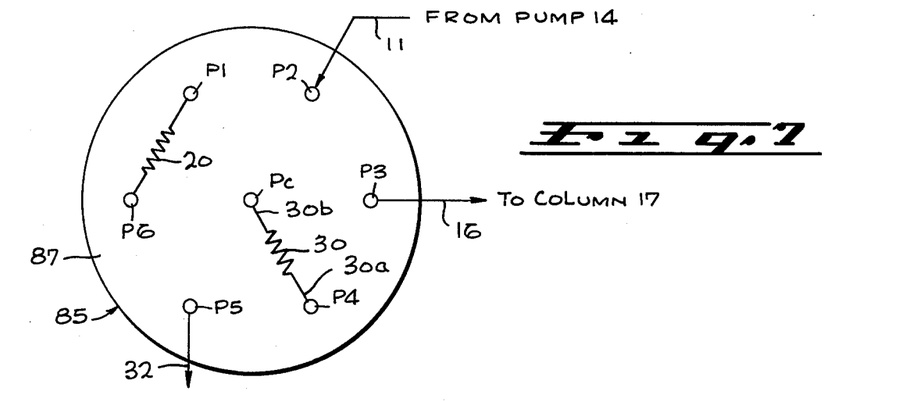
FIGS. 7–11 are diagrams useful in explaining another embodiment of the invention.

To overcome these potential disadvantages in accordance with the present invention, a new valve, which structurally differs from the one described in some aspects, is provided. This valve will be described in connection with FIGS. 7-11, in which elements like those previously described will be designated by like numerals. FIG. 7 is an elevational view of the outer side of the stator with seven external ports. Ports P1-P6 are assumed to be equally spaced from one another and from a centrally located port Pc. The sample loop 30 is connected between ports P4 and Pc. Since the ports are very close to one another, a very short tube with small ID can be used for sample loop 30. Thus, even when operating the valve in the upstream mode, as will be described hereinafter, peak spreading can be held to a minimum. The pump 14 is assumed to be connected by line 11 to port P2, while the column 17 is connected to port P5. The restrictor loop 20 is assumed to be connected to ports P1 and P6. As will be shown hereinafter, in this embodiment the restrictor loop 20 may not be required, since a path for solvent flow is provided between the source 12 and column 17 in either valve position (Load or Inject). In such a case ports P1 and P6 may be eliminated. However, for reasons to be explained hereinafter it may be desirable to include the restrictor loop 20 and therefore it will be assumed to be included for explanatory purposes.

Figure 8:
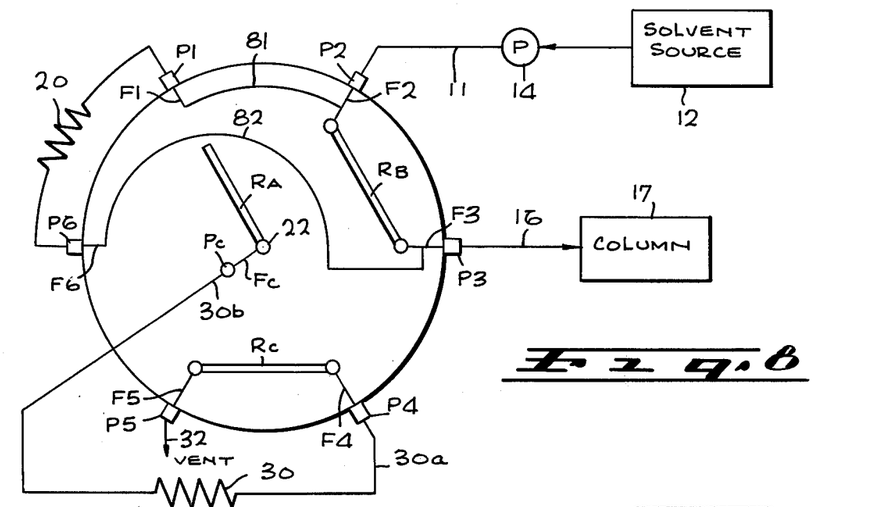
Figure 9:
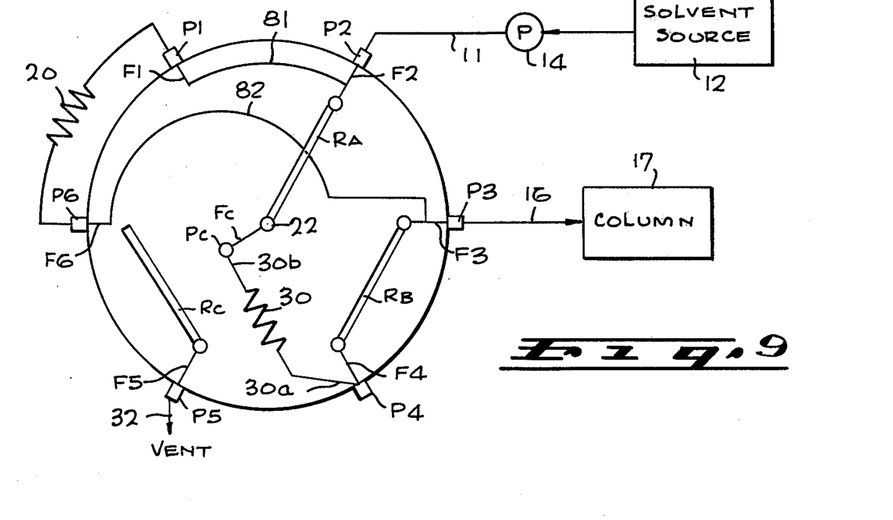

As shown in FIGS. 8 and 9, which are diagrams of the valve in the Load and Inject positions, respectively, the stator includes flow paths F1-F6 and Fc which extend from ports P1-P6 and Pc, respectively. However, only stator paths F2-F5 extend to the rotor as represented by the small circles, at their ends. Stator paths F1 and F6 do not extend to the rotor. Rather, they are respectively connected to stator paths F2 and F3 by very small internal slots 81 and 82, formed in the stator structure. As will be pointed out hereinafter these paths are easily formed in a plastic disc seal of the stator as very small slots or channels, thereby eliminating the need for relatively expensive external T-type junctions, which would have been required to connect restrictor loop 20 to lines 11 and 16 external to the valve. Slots 81 and 82 may be formed to have effectively zero dead volume.

In this embodiment with port Pc centrally located, both the port Pc and stator flow path Fc are typically axially aligned with cavity 22. However, for explanatory purposes Pc and Fc are shown off center. As will be pointed out hereinafter in connection with FIG. 10 the stator flow path Fc extends to the rotor and is always in flow communication with the end 22d of the needle cavity 22, opposite the sealed end 22u through which the syringe needle 27 or the plug 35 are inserted into the needle cavity.

As shown in FIGS. 8 and 9 the rotor includes three flow passages $R_A$, $R_B$ and $R_C$. Passage $R_A$ has one end which is always in communication with the needle cavity 22 and more importantly with the end of stator path Fc which abuts the rotor. In the Load position $R_A$ does not perform any function. In the same position $R_B$ provides a flow passage between stator flow paths F2 and F3. Thus, in the Load position practically all of the solvent flows to the column 17 from source 12 via $R_B$. Therefore, restrictor loop 20 is not needed for continuous solvent flow to the column in the Load position. However, such a loop 20 is desirable in the foregoing described embodiment, since therein restrictor loop 20 is the only means through which solvent can flow to the column when the valve is in the Load position. As shown in FIG. 8 in the Load position, $R_C$ provides a flow passage between F4 and F5, thereby enabling the end 30a of the sample loop 30 to be vented to the atmosphere. This enables a conventional rather than a high pressure syringe to be used for sample loading.

In the Inject position the rotor flow passages $R_A$, $R_B$ and $R_C$ are shown in FIG. 9. $R_A$ provides a flow path between F2 and Fc, while $R_B$ provides a flow path between F3 and F4. Thus, the solvent, pumped by pump 14 into the valve enters the valve through port P2, and therefrom it flows through stator flow path F2 and the rotor flow passage $R_A$ to the needle cavity 22. Therefrom it enters Fc and sample loop 30 (via end 30b) and pushes the previously loaded sample ahead of it. The solvent, together with the sample, flow through loop 30 and exit loop end 30a which is connected to P4. Therefrom they flow to the column via F4, $R_B$, F3, P3, and line 16, which connects the column 17 to valve port P3. In the Inject position $R_C$ does not perform any function. In the Load position only displaced solvent is present therein, which remains in $R_C$ and is subsequently ejected through vent 32 during a subsequent sample loading operation.

Figure 10:
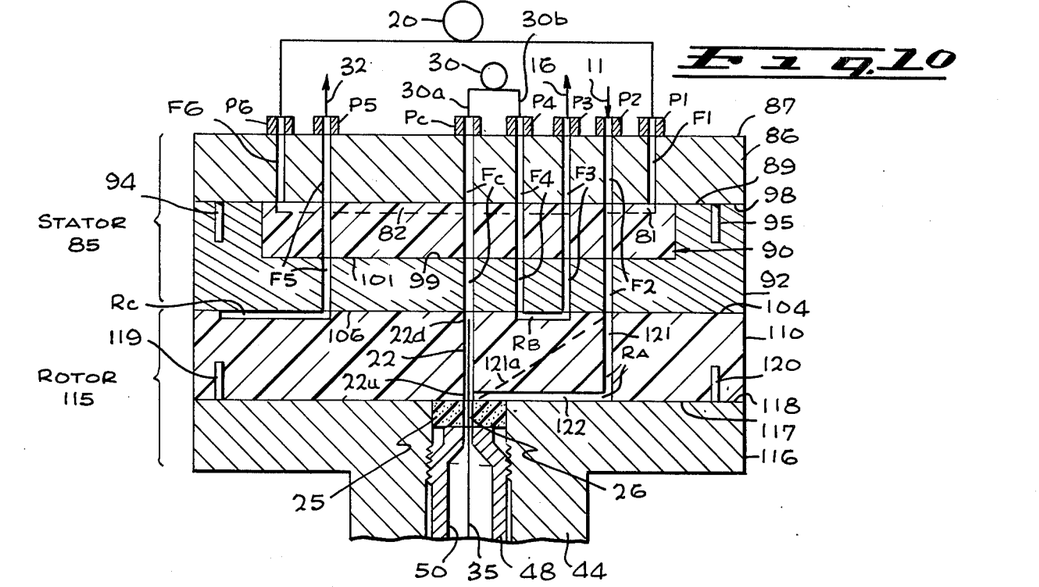
Figure 11:
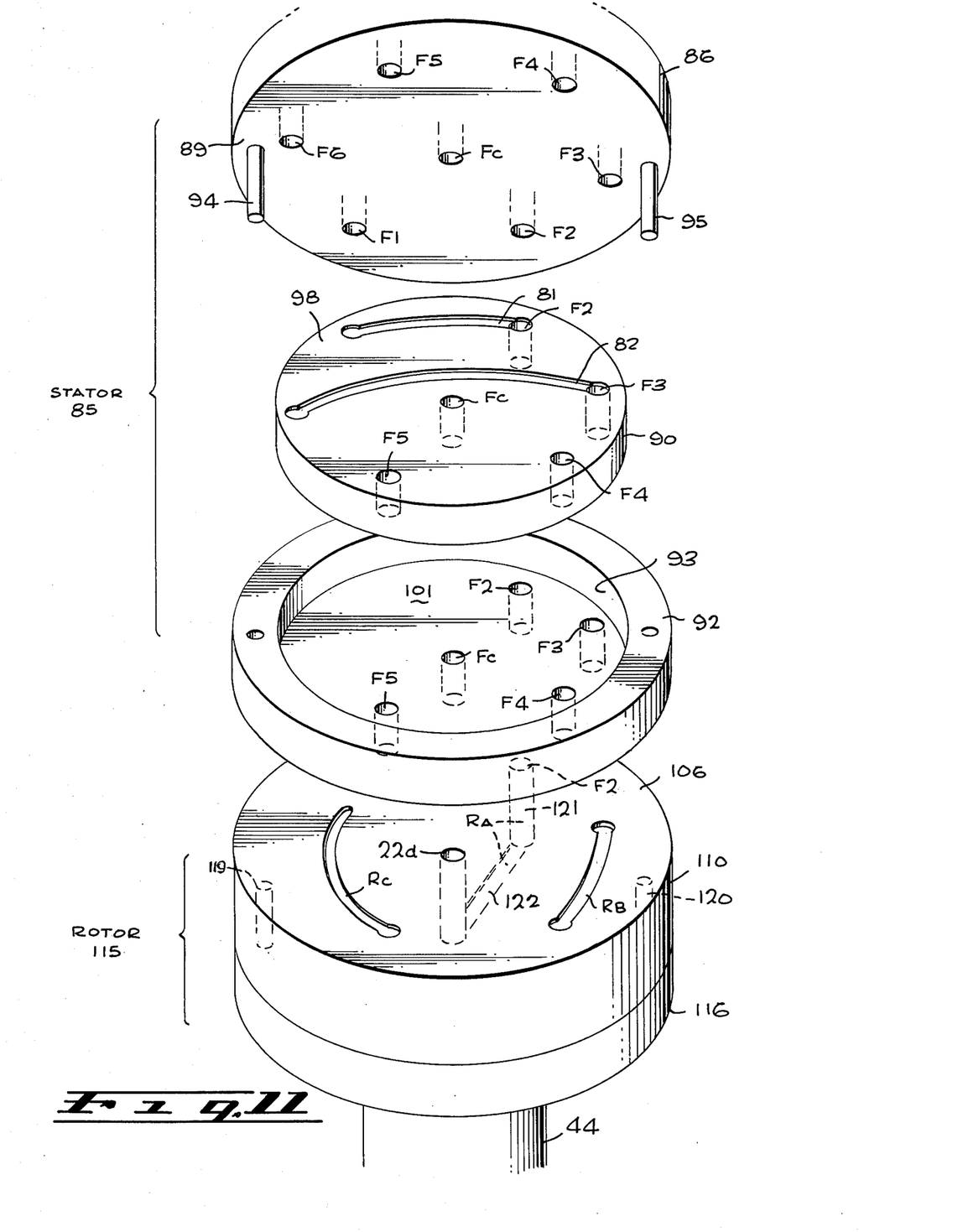

Attention is now directed to FIGS. 10 and 11 in connection with which an embodiment of the valve shown in FIGS. 7-9, which was actually reduced to practice, will be described. FIG. 10 is effectively a cross-sectional view of the valve with the rotor being shown in the Inject position. For explanatory purposes all the ports and their associated flow paths are shown side by side rather than circularly about center port Pc. FIG. 11 is an isometric expanded view of the parts shown in FIG. 10. Basically, the stator 85 includes a multiport unit 86 with the seven ports on its top side 87 as shown in FIG. 7. Extending from ports P1-P6 and Pc on side 87 toward a flat side 89 of unit 86 are the stator flow paths F1-F6 and Fc, respectively. Unit 86 is typically of stainless steel and paths F1-F6 and Fc are very small holes, e.g., 0.010 inch in diameter.

Associated with unit 86 and forming part of stator 85 are a stator seal 90 and a stator cover 92. The seal 90 is shown in the shape of a thin circular disc which is accommodated in an opening 93 in the stator cover 92. The stator cover 92 is aligned with the unit 86 by means of aligning pins 94 and 95. The seal is generally of a plastic-like material, e.g., an inert fluoropolymer, which is chemically inert and does not react with either the solvent or samples which may flow therethrough, and is capable of withstanding high pressure, e.g., 7000 psi. The stator unit 86 and the stator cover 92 are typically of metal, e.g., stainless steel, such as 316 SS. In one embodiment both the stator seal 90 and a rotor seal, to be described hereinafter, are formed of glass reinforced Tefzel with a chemical inertness approximately that of Teflon and glass and of sufficient mechanical strength to withstand high pressure, e.g., 7000 psi. As is known Tefzel and Teflon are materials available from Du Pont, Corporation.

When the stator is assembled the top face 98 of seal 90 abuts against side or face 89 of unit 86 and the seal face 99 is in tight contact with surface 101 of the opening 93 (see FIG. 11) in stator cover 92. The stator cover 92 terminates in a flat face 104 which comes in contact with the top face 106 of a rotor seal 110.

The stator's parts 86, 90 and 92, once assembled, do not change positions with respect to one another. As shown the stator seal 90 and cover 92 have holes drilled in them so that when the stator 85 is assembled stator flow paths F2-F5 and Fc extend through the entire stator 85 to face 104 of stator cover 92, i.e., to face 106 of rotor seal 110. However, stator flow paths F1 and F6, which extend from ports P1 and P6 respectively, to which the restrictor loop 20 is connected, extend only through unit 86, to the top face 98 of stator seal 92. As shown in FIGS. 10 and 11 very narrow slots or channels 81 and 82 are formed in the top surface 98 of the seal. Slot 81 extends between the ends of F1 and F2 at surface 89, while slot 82 extends between the end of F6 and F3. These slots form stator flow paths 81 and 82. It is thus seen that these slots 81 and 82 serve to interconnect the restrictor loop 20 to external lines 11 and 16 through the stator 85, thereby eliminating the need for two external T-junctions to couple loop 20 to these external lines. This point is quite significant. By merely forming two slots or channels in the stator seal 90 flow paths are provided between two different pairs of flow paths in the stator. Thus, by connecting loop 20 to ports P1 and P6, by means of channels 81 and 82 in the stator, the loop is effectively connected across ports P2 and P3, i.e., to lines 11 and 16 without external T-junctions. The channels 81 and 82 can be made to have practically zero dead volume.

In FIGS. 10 and 11 the valve's rotor is designated by 115. It includes a main rotor member 116 from which the rotor shaft 44 extends. Member 116 has a flat face 117 on which side or face 118 of the rotor seal 110 rests. As in the foregoing described embodiment the rotor shaft 44 accommodates a bushing 48 with its axial cavity 50. The bushing is threadable into the rotor shaft to control the pressure on cavity seal 25 and thereby control the size of the seal's opening 26. The rotor seal 110 is fixedly positioned and aligned with rotor member 116 by aligning pins 119 and 120. In operation, while stator 92 is stationary it is rotor 115 which is rotated between the two positions (Load and Inject) to align the rotor passages $R_A$, $R_B$ and $R_C$ with respect to the stator flow paths, extending to face 104 of stator cover 92.

In the present embodiment the needle cavity 22 is in the form of an axially aligned central hole extending through the rotor seal 110 between its opposite faces 106 and 118. The end of needle cavity 22 near face 118 is designated by 22u while its other end at face 106 is designated by 22d. At all times a flow path exists between the cavity end 22d and the stator flow path Fc which extends to face 104 of the stator cover 92.

As previously indicated the rotor seal 110 is generally formed of a plastic-type material, like stator seal 90. In the rotor seal 110 in addition to the needle cavity 22 the rotor flow passages $R_A$, $R_B$ and $R_C$ are also formed. In FIG. 10 they are shown by solid lines in the Inject position. Rotor passages $R_B$ and $R_C$ are shown for explanatory purposes as grooves or channels in face 106 of the rotor seal. In the Inject position, as shown in FIGS. 10 and 11, $R_B$ provides a flow path between F3 and F4. However, $R_C$ does not perform any function. Although one end of it is in communication with F5, the other end of $R_C$ or any point therealong does not come in contact with any of the other stator flow paths. In the Load position, as shown in FIG. 8, $R_B$ provides a flow path between F2 and F3, and $R_C$ provides a flow path between F4 and F5, thereby enabling the sample loop 30 to be vented to the atmosphere.

The rotor passage $R_A$ consists of a hole 121 extending through the rotor seal 110 and a channel 122 which extends from the end of this hole at rotor seal face 118 to the end 22u of the needle cavity. Such a rotor flow passage is desirable to insure the proper flushing out of any sample present in the needle cavity. In the Inject position the end of hole 121 at rotor seal face 106 is aligned with F2. However, in the Load position (see FIG. 8) $R_A$ does not perform any function since its hole 121 is not aligned with any of the stator flow paths. If desired $R_A$ may be formed as a slanted hole, extending from rotor seal face 106 to the needle cavity end 22u, as shown in FIG. 10 by a single dashed line, designated 121a. Also, each of passages $R_B$ and $R_C$ may be formed as a channel or groove in face 118 of the rotor seal 110, with two holes extending from the ends of each channel through seal 110 to its top face 106.

In operation in the Load position the sample is loaded by inserting a syringe needle 27, such as that shown in FIG. 1, into the cavity 22 through seal 25. The sample from the syringe needle flows into the sample loop 30 from the cavity 22 via Fc and Pc. Some sample may however remain in Fc and in the needle cavity 22. Also, some sample may even be present in $R_A$. Thereafter, the syringe needle 27 is withdrawn and the plug 35 is inserted (as shown in FIG. 10). Then the valve is switched to the Inject position. In it hole 121 of $R_A$ is aligned with F2. In the upstream mode of operation solvent flows from source 12 into F2 through port P2 and from F2 it flows through hole 121, channel 122 (i.e., $R_A$) into the needle cavity 22 near end 22u. The solvent displaces any sample left in $R_A$ or cavity 22 and pushes the sample ahead of it. The solvent at high pressure with any sample traces flows from cavity 22 into Fc and therefrom through port Pc, sample loop 30, port P4, F4, rotor passage $R_B$, F3 and out of port P3, which is assumed to be connected to the column 17 by line 16. Thus, all the sample is ejected out of the sample loop 30 through loop end 30b, which is opposite loop end 30a through which the sample was loaded into the sample loop in the Load position. It should be stressed that since ports Pc and P4 to which the sample loop 30 is connected are very close to one another a very short sample loop with a very small internal diameter can be used. Thus, even though the valve is operated in an upstream mode of operation peak spreading of even extremely small samples, one or more microliters, may be held to a minimum.

It should be stressed that in the valve just described solvent flows from source 12 to column 17 in either valve position. In the Load position the solvent flows through rotor passage $R_B$. In the Inject position it flows from the source to the column through $R_A$, the needle cavity 22, sample loop 30 and $R_B$. The only interruption in the continuous solvent flow to the column may occur during the time the valve is switched between the two positions. This time is extremely short. In a system in which an interruption in the flow of solvent to the column cannot be tolerated even during the extremely short valve switching time, the restrictor loop 20 and the stator flow paths 81 and 82 are required. If, however, such brief solvent flow interruption can be tolerated, with the flow being regarded as substantially continuous, the restrictor loop 20 can be eliminated, thus eliminating the need for ports P1 and P6, and the stator flow paths F1, F6, 81 and 82. In such a case a valve with only five ports P2–P5 and Pc, i.e., a five port valve, is required.

Hereinbefore (see FIG. 10) the valve was described with port Pc and Fc being axially aligned with the cavity 22 along the valve axis of rotation. If desired the port Pc may be off center. Also stator path Fc need not be axially aligned. However, its end at face 104 of the stator cover 92 must be aligned with end 22d of the needle cavity 22. The latter is preferably axially aligned so that regardless of the valve position the needle cavity extends along the valve axis of rotation and its end 22d is always in flow communication with stator flow path Fc. However, if desired the needle cavity may be aligned parallel to the axis of rotation slightly off center. However, its end 22d must be aligned with the end of Fc irrespective of valve position. It should be pointed out that in this valve if one regards the cavity end 22u as an inlet through which sample is loaded into the valve, the sample loop 30 is not directly connected to this inlet. Rather, it is effectively connected thereto through the entire length of cavity 22, stator path Fc and external port Pc.

Hereinbefore the valve was described in an upstream mode of operation. If desired it can be operated in the downstream mode by connecting line 11 from pump 14 to port P3 and by connecting line 16 to which column 17 is connected to port P2. In such a mode the sample, loaded into sample loop 30 via the needle cavity 22 and Fc, will be ejected from the loop 30 from the sample loop end 30a through which the sample was loaded into the loop.

Figure 12:
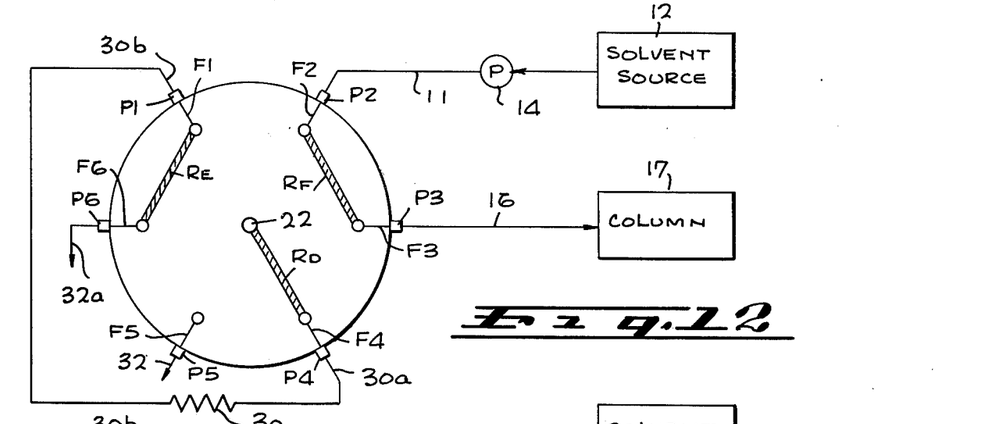
FIGS. 12–14 are diagrams useful in explaining yet another embodiment of the invention.
Figure 13:
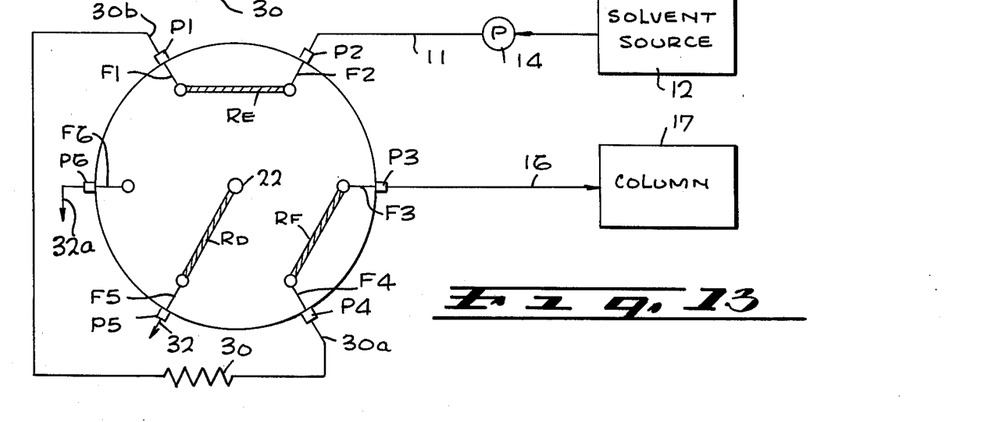

In either of the two valves, hereinbefore described, the solvent at high pressures flows through the needle cavity in the Inject position. Thus, the cavity end 22u must be sealed. This is achieved by inserting plug 35 through seal 25 into the cavity prior to switching the valve to the Inject position. Attention is now directed to a third embodiment of the two-position valve in which the need for the plug 35 is eliminated. In this embodiment the needle cavity 22 is not in the path of the high pressure solvent in the Inject position. This embodiment will be described in connection with FIGS. 12 through 14 for a downstream mode of operation. FIGS. 12 and 13 show the valve in the Load and Inject positions, respectively, while FIG. 14 is a partial cross-sectional view of the valve in the Load position.

Figure 14:
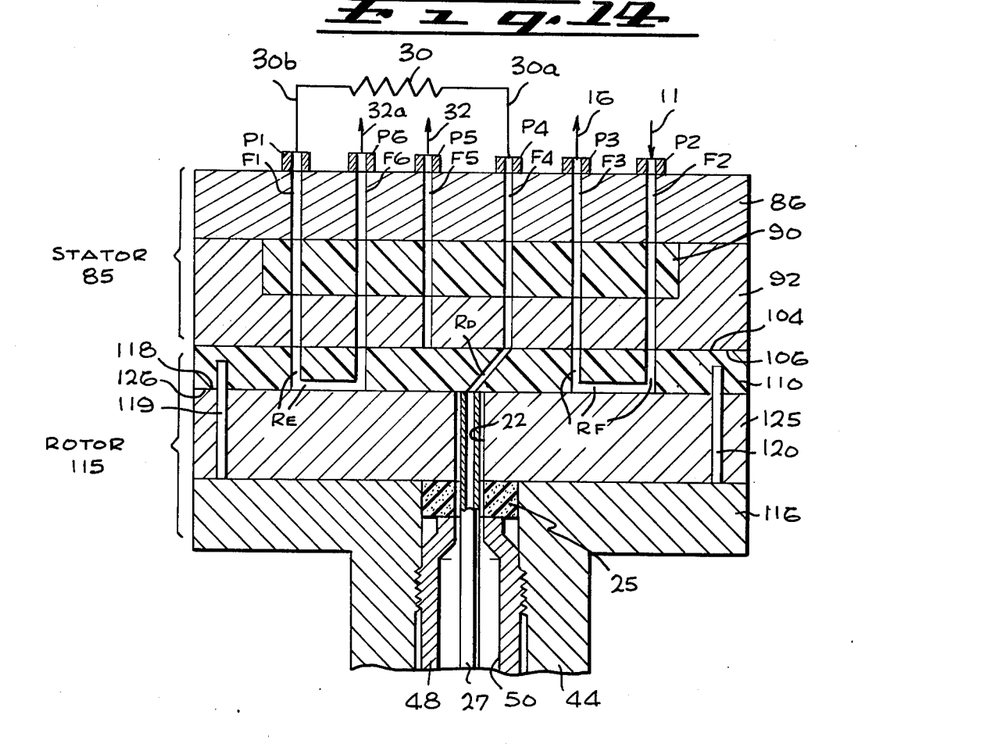

This valve is a six-port valve with all of the stator flow paths F1–F6 extending to the rotor seal 110 (see FIG. 14). In this valve the sample loop 30 is connected between ports P1 and P4. Port P6, like port P5, is vented to the atmosphere. A vent line 32a is shown connected to port P6. The valve includes three rotor flow passages, designated $R_D$, $R_E$ and $R_F$. In the Load position $R_D$ connects the needle cavity to end 30a of the sample loop 30, while the other loop end 30b is vented, due to the flow path provided by $R_E$ between F1 and F6. $R_F$ provides a flow path for solvent between source 12 and column 17.

After the sample is loaded into the sample loop 30 through loop end 30a, the valve is switched to the Inject position. In this position (FIG. 13) $R_E$ interconnects F1 and F2, and $R_F$ interconnects F3 and F4. Thus, solvent flows through the sample loop 30 so as to eject the sample onto column 17 from the loop 30 through the sample loop end 30a, through which the sample was loaded into the loop. In the Inject position $R_D$ connects the needle cavity 22 to vent line 32 through F5 and P5. Thus, in this valve the needle cavity is not present in the flow path of the high pressure solvent. Rather, it is vented to the atmosphere. Consequently, the need for plug 35 is eliminated. In the presently described embodiment some sample loss may occur. This is due to the fact that the sample is loaded in the Load position into the sample loop 30 through $R_D$, which is not part of the solvent flow path in the Inject position. Therefore, any amount (volume) of sample in $R_D$ may be lost. However, $R_D$ may be formed to have a minimal volume so as to minimize the amount of lost sample. In one embodiment $R_D$ is a hole in the rotor seal 110 of 0.35mm in diameter and only 4.4mm long, thereby having a total volume of less than 0.5μl.

Attention is now directed to FIG. 14, wherein elements like those previously described are designated by like numerals. In this embodiment, unlike that described before in connection with FIG. 11, the needle cavity 22 is not formed in rotor seal 110. Rather, it is formed in a rotor section 125 which together with rotor seal 110 are aligned with rotor structure 116 by the alignment pins 119 and 120. As shown in FIG. 14 the rotor passages $R_D$, $R_E$ and $R_F$ are formed in the rotor seal 110. $R_D$ is shown as a hole extending from the opposite seal faces 106 and 118. The latter face is in intimate contact with the top face or side 126 of rotor section 125. $R_E$ is shown as a groove in seal face 118 with two holes extending from the groove ends to seal face 106. $R_F$ is similarly formed as a groove in seal face 118 and two holes extending from its ends to seal face 106. However, if desired, each of $R_E$ and $R_F$ may be formed as a groove in seal face 106.

The needle cavity diameter is sufficient to provide sufficient clearance for the syringe needle 27. The needle outer diameter (OD) is greater than that of the hole which forms $R_D$ in seal 110. When the syringe 27 is inserted into the cavity 22 and its front end abuts against rotor seal 110. By holding the syringe so that the front end or tip of the needle 27 continues to abut against the rotor seal 110 the needle tip acts as a seal 22, so that all the sample ejected from the needle flows into $R_D$ and therefrom to the sample loop 30 through F4 and P4. The effective seal formed by the needle tip abutting against rotor seal 110 prevents ejected sample from flowing into the needle cavity. Preferably, the syringe needle is held within the cavity 22 unitl the valve is switched to the Inject position, in order to prevent even minute amounts of sample from spilling out of $R_D$ into the cavity.

As shown in FIG. 13 in the Inject position $R_D$ is connected to the vent line 32 (via F5 and P5). The flow passage $R_D$ may be cleansed from any sample remanents therein, by flushing $R_D$ with solvent when $R_D$ is vented to the atmosphere in the Inject position, as shown in FIG. 13. Since the needle cavity is not in the solvent flow path in the Inject position, if desired the cavity seal 25 (see FIG. 14) may be eliminated.

It should be pointed out that if desired the valve shown in FIGS. 12-14 may be operated in an upstream mode. This can be achieved by connecting line 11 to P3 and line 16 to P2. It should also be pointed out that if desired a restrictor loop 20 may be added to the valve to provide solvent flow to the column during the brief valve switching period. This can be achieved by using two external T-junctions to connect the restrictor loop 20 to lines 11 and 16. Also, it can be achieved by adding two more ports (such as P1 and P6 in FIG. 8) to the valve and provide the stator with internal flow paths (such as 81 and 82) between the two ports and stator flow paths F2 and F3, as hereinbefore described in connection with FIGS. 8-11.

Any of the above described valves may be used to inject a sample into a stream of solvent at high pressure. The sample volume may vary from an extremely small volume, e.g., 1μl or more up to a maximum, which depends on the sample loop volume. When the amount of sample which is to be loaded is measured by the syringe markings the sample loop should have a sufficient internal volume to insure that in the Load position none of the loaded sample reaches the vented end of the loop. In the previously described embodiments of the valves none of the sample is lost. In the last described embodiment some sample is lost. However, as previously pointed out by making the volume of rotor passage $R_D$ very small the lost sample volume may be held to a minimum, e.g., 0.5μl. It should be appreciated however that if desired that instead of using the syringe markings for sample volume measurement the sample loop may be completely filled. Such complete loop filling is possible with all the embodiments. However, it should be realized that appreciable sample loss will occur since excess sample will spill out of the vented end of the sample loop.

Figure 15:
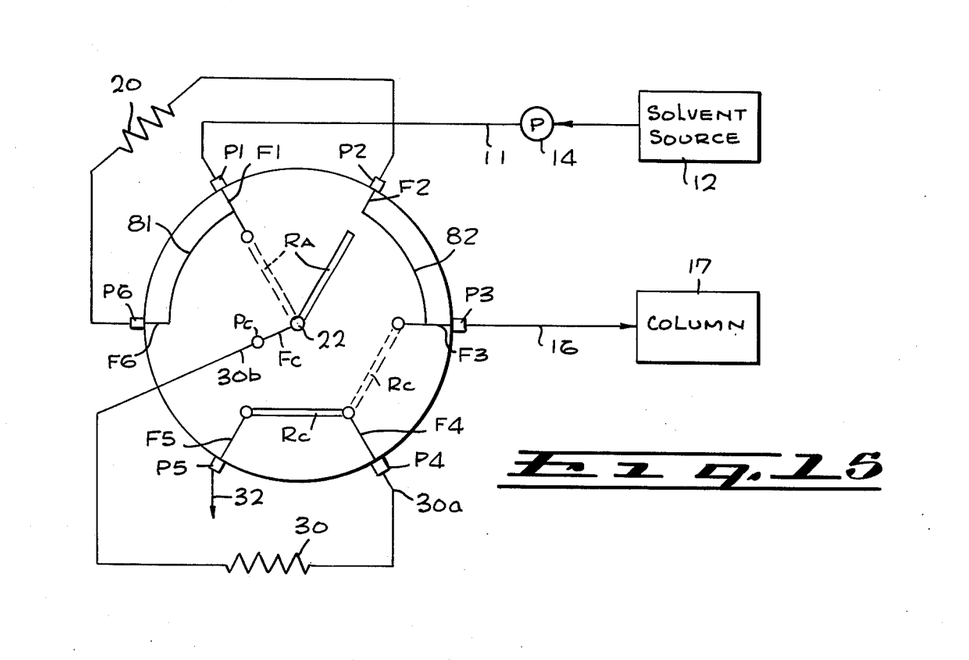
FIG. 15 is a diagram showing a modification of the embodiments described in FIGS. 7–11.

Although particular embodiments of the invention have been described and illustrated herein, it is recognized that modifications and variations may readily occur to those skilled in the art. For example, the valve described in connection with FIGS. 7-11 is shown including three rotor passages $R_A$, $R_B$ and $R_C$, and the valve is assumed to be rotated clockwise (CW) between the Load and Inject positions. If desired passage $R_B$ may be eliminated as shown in FIG. 15 without affecting the valve operation. In FIG. 15 the source is shown connected to P1 and the restrictor loop 20 to ports P2 and P6. In FIG. 15 the rotor passages $R_A$ and $R_C$ in Load position are shown in solid lines, and in dashed lines in the Inject position. $R_A$ performs the same functions as hereinbefore described. $R_C$ provides the path for venting the loop 30 to the atmosphere in the Load position. Then when the valve is rotated CCW it ($R_C$) interconnects ports P4 and P3. It should be pointed out that in the embodiment shown in FIG. 15 solvent flows to the column through restrictor loop 20 at all times. Clearly, if the solvent flow to the column can be interrupted during the entire Load position, restrictor loop 20 can be eliminated, thus eliminating the need for ports P2 and P6, thereby reducing the valve to a five-port valve.

Other modifications and variations may readily occur to those familiar in the art. Therefore, it is intended that the claims be interpreted to cover all such modifications and equivalents.

The embodiments of the invention in which an exclusive property or privilege is claimed are defined as follows:

1. For use with a source of liquid from which liquid flows at a first pressure to a liquid receiver a rotary valve positionable in either a first position definable as a load position or a second position definable as an inject position, for injecting a liquid sample into the stream of liquid from said source to said receiver, the valve comprising:

a stationary stator including a plurality of external ports and a corresponding plurality of internal liquid flow paths in communication with said ports said ports including a pair of ports connectable to said source and receiver, and further including a group of $n$ ports, where $n$ is an integer not less than 3;

an external conduit defining a sample loop through which liquid is adapted to flow, said conduit being of a selected length and internal diameter and being connected to first and second of said $n$ ports, said $n$ ports including a third port exposed to a second pressure less than said first pressure;

rotor means rotatable with respect to said stator about a selected axis to thereby position said valve in either said load or inject position, and including a cavity having first and second open ends, said first open end being in flow communication with said first external port irrespective of the valve position, said rotor means further including a plurality of rotor flow passages for providing a liquid flow path between the stator flow paths in communication with said second and third ports, only when the valve is in said load position and for providing a liquid flow path between the pair of ports to which said source and receiver are connected through said cavity and said sample loop, when said valve is in the inject position;

seal means for sealing the cavity second end, said seal means defining an opening accessible from the valve exterior for facilitating the insertion of a syringe needle into said cavity therethrough for injecting a liquid sample into said sample loop through said cavity; and plug means for effectively closing the opening of said seal means, said seal means with said plug means being adapted to withstand said first pressure when liquid flows through said cavity at said selected pressure when said valve is in said inject position, said plug means comprising an elongated wire having a front portion thereof insertable into said cavity through the seal means opening to thereby close the latter, and a lockable plug holder connected to the wire end opposite the front portion which is insertable into said cavity.

2. The valve as described in claim 1 wherein said rotor means includes at least first and second rotor flow passages, said first rotor passage extending from the second end of said cavity for providing a path for solvent flow through the cavity when said valve is in said inject position and said second rotor passage providing a solvent flow path between said second and third ports when said valve is in said load position.

3. The valve as described in claim 1 wherein said group of $n$ ports further includes fourth and fifth external ports, with said stator including internal flow channels for connecting the stator flow paths which are in communication with the fourth and fifth ports with the stator flow paths in communication with said pair of ports to which the source and receiver are connectable, and an external loop of preselected internal diameter connected to said fourth and fifth ports.

4. The valve as described in claim 3 wherein said rotor means includes at least first and second rotor flow passages, said first rotor passage extending from the second end of said cavity for providing a solvent flow path through the cavity when said valve is in said inject position and said second rotor passage providing a solvent flow path between said second and third ports when said valve is in said load position.

5. The valve as described in claim 1 wherein said rotor means defines first, second, and third rotor flow passages, said first rotor passage extending substantially from the cavity second end to a stator internal path which is in communication with one of the pair of ports to which the source or receiver is connected, only when said valve is in said inject position, with said second rotor passage extending between the stator paths in communication with the second and third ports only when said valve is in said load position, and said third rotor passage extending between the stator paths in communication with said pair of ports when the valve is in said load position and extending between the stator path in communication with said second port and the stator path in communication with the other of said pair of ports when the valve is in said inject position.

6. The valve as described in claim 5 wherein said group of $n$ ports further includes fourth and fifth external ports, with said stator including internal flow channels for connecting the stator flow paths which are in communication with the fourth and fifth ports with the stator flow paths in communication with said pair of ports to which the source and receiver are connectable and an external loop of preselected internal diameter connected to said fourth and fifth ports.

7. The valve as described in claim 1 wherein said cavity is substantially axially aligned along the rotor's axis of rotation.

8. For use with a source of liquid from which liquid flows at a first pressure to a liquid receiver a rotary valve, positionable in either a first position, definable as a load position, or a second position, definable as an inject position, for injecting a liquid sample into the stream of liquid from said source to said receiver, the valve comprising:
a stationary stator including a plurality of external ports and a corresponding plurality of internal liquid flow paths in communication with said ports, said ports including a pair of ports connectable to said source and receiver, and further including a group of $n$ ports, where $n$ is an integer not less than 4;
an external conduit defining a sample loop through which liquid is adapted to flow, said sample loop being of a selected length and internal diameter and being connected to first and second of said $n$ ports, said $n$ ports including at least third and fourth ports exposed to a second pressure, less than said first pressure; and
rotor means rotatable with respect to said rotor about a selected axis to thereby position said valve in either said load or inject position, and including a cavity having first and second open ends, said rotor means further including first, second and third rotor flow passages, said first rotor passage providing a liquid flow path between the stator internal flow paths in communication with said first external port and the first end of said cavity only when said valve is in said load position, and providing a flow path between the first end of said cavity and said fourth port when the valve is in said inject position, said second rotor passage providing a flow path when said valve is in said load position between the internal flow paths in communication with said second and third ports, and further providing a flow path between the internal paths in communication with said second port and one of said pair of ports when the valve is in said inject position, said third rotor passage providing a flow path between the internal flow paths which are in communication with said pair of ports when the valve is in the load position, and further providing a flow path between the internal flow paths in communication with said first port and the other of said pair of ports when said valve is in said inject position, said cavity, being accessible from the valve exterior through the second open end thereof for facilitating the injection of a sample into said sample loop through said first rotor passage when said valve is in said load position.

9. The valve as described in claim 8 wherein said cavity is an axial cavity substantially aligned with the rotor's axis of rotation, and first rotor passage has a first end in communication with the cavity first end irrespective of valve position, and a second opposite end which is in communication with the stator internal path extending to said first external port only when said valve is in said load position.

10. The valve as described in claim 9 wherein said first rotor passage is a hole of a first preselected diameter and said cavity has an internal diameter greater than said first diameter.

11. The valve as described in claim 10 wherein the center of the hole at the first end of said first rotor passage is substantially located on the axis of rotation.

12. For use in combination with a source of liquid from which liquid flows at a selected pressure greater than atmospheric pressure to a liquid receiver a rotary valve, positionable in either a first position, definable as a load position, or a second position, definable as an inject position, for injecting a liquid sample into the liquid stream from said source to said receiver, the valve comprising:
a stator including a plurality of external ports and a corresponding plurality of internal liquid flow paths in communication with said ports, said ports including first and second ports connectable to said receiver and source, respectively, a third port vented to atmospheric pressure, and a fourth port; an external conduit defining a fixed length sample loop having a first end connected to said fourth port and a second opposite end;

rotatable rotor means defining a needle cavity connected to the sample loop second end, and defining a first end and an opposite second end, said rotor means further defining first and second rotor flow passages, said first rotor passage providing a flow path between the cavity first end to the stator internal path in communication with said second port only when said valve is in said inject position, and said second rotor passage providing a flow path between the stator internal paths in communication with said third and fourth ports when said valve is in said load position, and between the stator internal paths in communication with said first and fourth ports when said valve is in said inject position, said rotor means further including seal means for sealing the cavity first end, said seal means defining an opening accessible from the valve exterior for facilitating the insertion of a syringe needle into said cavity therethrough for injecting a liquid sample into said sample loop through said cavity;

plug means for effectively closing the opening of said seal means, said seal means with said plug means being adapted to withstand said selected pressure when liquid flows through said cavity at said selected pressure when said valve is in said inject position, said rotor means being rotatable about a selected axis, with said needle cavity being an elongated cavity axially aligned with said selected axis.

13. The combination as described in claim 12 wherein the second end of said sample loop is connected to said cavity near the cavity first end adjacent said seal means, said needle cavity being an elongated cavity having an inner diameter only sufficiently large to accommodate the syringe needle therein, with substantially all of the sample injected into the cavity through said needle passing in the cavity around said needle to said sample loop.

14. The combination as described in claim 13 wherein said plug means comprise an elongated wire having a front portion thereof insertable into said cavity through the seal means opening to thereby close the latter, and a lockable plug holder connected to the wire end opposite the front portion which is insertable into said cavity, said valve further including means connected to said rotor means for locking the plug holder thereto to retain the wire front portion in said cavity when said valve is in said inject position and the liquid flowing in said cavity is at said selected pressure.

15. For use with a source of liquid from which liquid flows at a first pressure to a liquid receiver a rotary valve positionable in either a first position definable as a load position or a second position definable as an inject position, for injecting a liquid sample into the stream of liquid from said source to said receiver, the valve comprising:

a stationary stator including a plurality of external ports and a corresponding plurality of internal liquid flow paths in communication with said ports, said ports including a pair of ports connectable to said source and receiver, and further including at least additional first, second and third ports;

an external conduit defining a sample loop through which liquid is adapted to flow, said conduit being of a selected length and internal diameter and being connected to said first and second ports, said third port being exposed to a second pressure less than said first pressure;

rotor means rotatable with respect to said stator about a selected axis to thereby position said valve in either said load or inject position, and including a cavity having first and second open ends, said first open end being in flow communication with said first external port irrespective of the valve position, said rotor means further including first and second rotor flow passages, said rotor flow passages providing a liquid flow path between the stator flow paths in communication with said second and third ports. When the valve is in said load position and a liquid flow path between the stator flow paths in communication with said second port and one of the pair of ports when the valve is in said inject position and a second rotor flow passage for providing liquid flow path between the stator flow path which is in communication with the other of said pair of ports and said cavity only when the valve is in said inject position, said rotor means further including seal means for sealing the cavity second end, said seal means defining an opening accessible from the valve exterior for facilitating the insertion of a syringe needle into said cavity therethrough for injecting a liquid sample into said sample loop through said cavity; and plug means for effectively closing the opening of said seal means, said seal means with said plug means being adapted to withstand said first pressure when liquid flows through said cavity at said selected pressure when said valve is in said inject position, said plug means comprising an elongated wire having a front portion thereof insertable into said cavity through the seal means opening to thereby close the latter, and a lockable plug holder connected to the wire end opposite the front portion which is insertable into said cavity.

16. The valve as described in claim 15 wherein the stator includes fourth and fifth ports and internal flow channels for connecting the stator flow paths which are in communication with the fourth and fifth ports with the stator flow paths in communication with said pair of ports to which the source and receiver are connectable, and an external loop of preselected internal diameter connected to said fourth and fifth ports.

* * * * *